(12) United States Patent
Mohri (10) Patent No.: US 7,116,234 B2
(45) Date of Patent: Oct. 3, 2006

(54) DROWSINESS DETECTING DEVICE AND WAKING DEVICE OPERATIVELY CONNECTED WITH THE SAME

(75) Inventor: Kaneo Mohri, Aichi (JP)

(73) Assignee: Japan Science and Technology Agency, Kawaguchi (JP)

( * ) Notice: Subject to any disclaimer, the term of this patent is extended or adjusted under 35 U.S.C. 154(b) by 117 days.

(21) Appl. No.: 10/487,948

(22) PCT Filed: Mar. 31, 2003

(86) PCT No.: PCT/JP03/04084

§ 371 (c)(1),
(2), (4) Date: Mar. 5, 2004

(87) PCT Pub. No.: WO03/084403

PCT Pub. Date: Oct. 16, 2003

(65) Prior Publication Data

US 2004/0233060 A1 Nov. 25, 2004

(30) Foreign Application Priority Data

Apr. 10, 2002 (JP) ............................. 2002-107337

(51) Int. Cl.
*G08B 23/00* (2006.01)

(52) U.S. Cl. ...................... 340/575; 340/576; 340/643; 340/547

(58) Field of Classification Search .............. 340/575, 340/576, 573.1, 573.7, 546, 544, 545, 547, 340/643, 825.72; 600/26–28
See application file for complete search history.

(56) References Cited

U.S. PATENT DOCUMENTS

| 5,064,410 A | * | 11/1991 | Frenkel et al. ................ 600/26 |
| 5,402,109 A | * | 3/1995 | Mannik ...................... 340/575 |
| 6,006,994 A | * | 12/1999 | Plesko ................... 235/462.32 |

FOREIGN PATENT DOCUMENTS

| JP | 58-173535 | | 10/1983 |
| JP | 2-220627 | | 9/1990 |
| JP | 8-300977 | | 11/1996 |
| JP | 2000157503 A | * | 6/2000 |
| JP | 2002-78684 | | 3/2002 |

* cited by examiner

*Primary Examiner*—Jeffery Hofsass
*Assistant Examiner*—Edny Labbees
(74) *Attorney, Agent, or Firm*—Oblon, Spivak, McClelland, Maier & Neustadt, P.C.

(57) ABSTRACT

A prompt, accurate and highly practical drowsiness detecting device and a waking device operatively connected with the same are provided.

Drowsiness of a vehicle driver or the like is detected to wake him/her up to prevent the drowsiness from causing an accident. A waveform of blinking is detected by a stress-impedance effect sensor head (1) positioned on a temple bow of a glasses frame in the vicinity of his/her temple, and the drowsiness is determined by a microcomputer (2). Waking him/her up is accomplished by a milligauss AC magnetic field generator (4).

3 Claims, 7 Drawing Sheets

ND WAKING DEVICE OPERATIVELY
DROWSINESS DETECTING DEVICE AND WAKING DEVICE OPERATIVELY CONNECTED WITH THE SAME

TECHNICAL FIELD

The present invention relates to a drowsiness detecting device and a waking device operatively connected with the same contributing to prevention of traffic accidents or industrial accidents by detecting the drowsiness of vehicle drivers or security surveillance personnel at plants and waking them up while they are on duty.

BACKGROUND ART

Hitherto, diverse attempts have been reported in developing drowsiness sensors intended for vehicle drivers, including (1) one adapted to detect the images of drivers' faces by cameras to determine their drowsiness by the motions of their eyelids, (2) one adapted to monitor heartbeats or pulses, and (3) one adapted to monitor changes in electrical resistance of the skin between wrists and little fingers. All of them, however, still have many disadvantages to be overcome and have not been put to practical use.

More specifically, the abovementioned methods have, for example, the following disadvantages: (1) the image monitoring method has a disadvantage in that a sudden change in the amount of light, such as during daytime and night, makes it difficult to recognize images, (2) the heartbeat or pulse monitoring method is disadvantageous in that it is difficult to distinguish between composure of experienced drivers and drowsiness, and (3) the method for monitoring changes in the electrical resistance of skin has no scientific basis and it is difficult to determine such changes, depending on humidity of skin.

Meanwhile, the present inventor has previously invented a drowsiness sensor (registration number 2009287) based on the fact that if eyelids close for 0.5 second or more, then it indicates heavy drowsiness, independently of differences among individuals.

DISCLOSURE OF INVENTION

The aforementioned drowsiness sensor, however, is adapted to detect the magnetic field of very small magnets attached eyelids that move together with the eyelids by a magnetic field sensor fixed on a glasses frame, presenting an actual disadvantage of the need for attaching the magnets.

Other proposed conventional methods for waking drowsy persons up after detecting and determining their drowsiness use electronic sound alarms or generate pungent smells, such as a lemon smell. All of these methods, however, depend on stimulation from outside sensory organs, taking time to effect physiological awakening. In addition, drowsiness may immediately deepen or the effectiveness may significantly vary, depending on differences among individuals. For these reasons, the methods have not yet been brought into actual use.

The present invention has been made in view of the above, and it is an object of the present invention to provide a prompt, accurate and highly practical drowsiness detecting device and a waking device operatively connected with the same.

To this end, the present invention provides the following.

[1] A drowsiness detecting device equipped with a high-sensitivity stress sensor attached to a temple bow of a glasses frame at a position thereof in the vicinity of a temple of a user, and a microcomputer that detects a blinking motion of the user's eyelids from information supplied from the high-sensitivity stress sensor and determines the drowsiness of the user on the basis of the detected information.

[2] In the drowsiness detecting device described in [1] above, the high-sensitivity stress sensor is a stress sensor combining stress-impedance effect of an amorphous magnetostrictive thin wire and a CMOS multivibrator circuit.

[3] A drowsiness detecting and waking device equipped with a high-sensitivity stress sensor attached to a temple bow of a glasses frame at a position thereof in the vicinity of a temple of a user, a microcomputer that detects a blinking motion of the user's eyelids from information supplied from the high-sensitivity stress sensor and determines the drowsiness of the user on the basis of the detected information, and a waking device operating on the basis of a drowsiness signal from the microcomputer.

[4] In the drowsiness detecting and waking device described in [3] above, the high-sensitivity stress sensor is a stress sensor combining stress-impedance effect of an amorphous magnetostrictive thin wire and a CMOS multivibrator circuit.

[5] The drowsiness detecting and waking device described in [3] above, further equipped with a milligauss ultra-low frequency AC magnetic field generator driven on the basis of a drowsiness signal from the microcomputer, wherein a magnetic field generated by the milligauss ultra-low frequency AC magnetic field generator is applied to the brain of the user.

[6] In the drowsiness detecting and waking device described in [5] above, a coil and a driving circuit for generating the milligauss ultra-low frequency AC magnetic field are disposed in the vicinity of the brain of the user.

[7] In the drowsiness detecting and waking device described in [5] above, a coil and a driving circuit for generating the milligauss ultra-low frequency AC magnetic field are disposed in the vicinity of a temple of the user.

The present invention has been constructed by improving a supersensitive stress sensor previously invented by the present inventor (stress-impedance effect device in Japanese Unexamined Patent Application Publication No. 10-170355) for practical use, and by fixing it on a glasses frame such that a sensor head thereof is pressed against the vicinity of a temple of a driver's head. With this arrangement, eyelid motions are detected without attaching magnets on eyelids, and drowsiness is determined by a microcomputer.

Furthermore, the present invention has been constructed using a principle that is utterly different from a conventional waking method. According to the present invention, a micro AC magnetic field in the order of milligauss is applied to activate in vivo water molecules or vital ions for the purpose of waking effect. The new waking method has been invented by waking experiments on the basis of "Minute pulse magnetic field generator, and blood circulation promotion, immune resistance enhancement and anagenesis system using it" (Patent Application No. 2001-286611) already invented by the present inventor.

BEST MODE FOR CARRYING OUT THE INVENTION

An embodiment of the present invention will now be explained with reference to the accompanying drawings.

Figure 4:
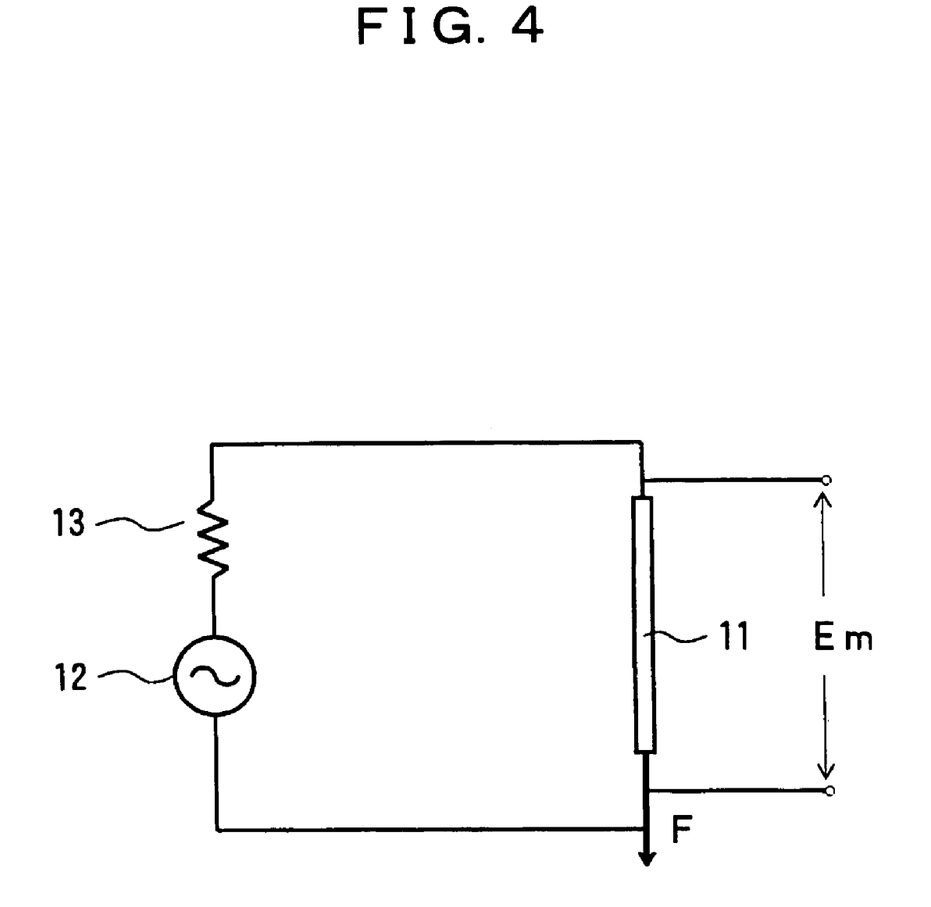
FIG. 4 shows a high-sensitivity stress detector in accordance with the present invention and a circuit diagram thereof.
Figure 5:
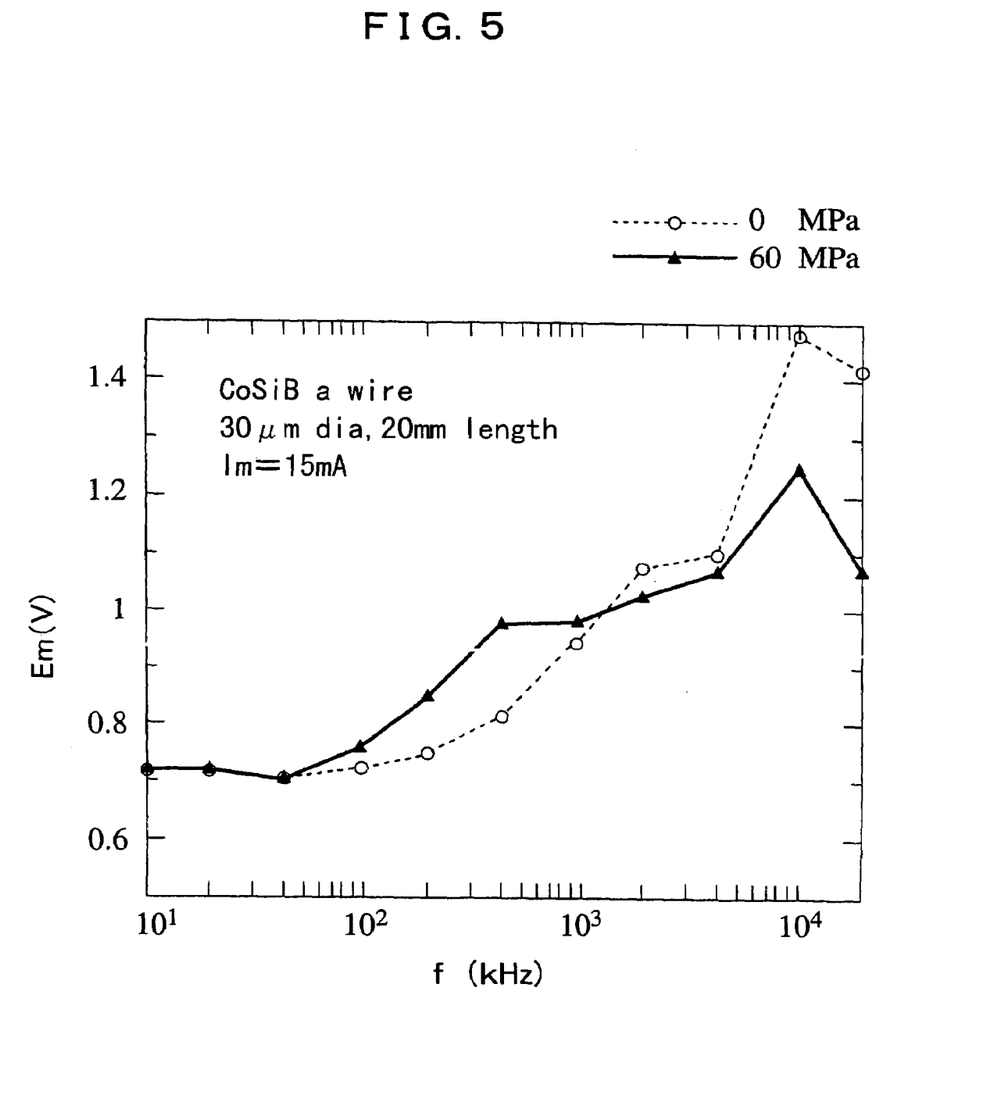
FIG. 5 is a frequency characteristic diagram showing changes in voltage amplitude caused by stress of the high-sensitivity stress detector in accordance with the present invention (part 1).

FIG. 4 is a high-sensitivity stress detector in accordance with the present invention and a circuit diagram thereof. FIG. 5 is a frequency characteristic diagram showing changes in voltage amplitude caused by stress of the high-sensitivity stress detector (part 1).

In FIG. 4, reference numeral 11 denotes a negative magnetostrictive $Co_{22.5}Si_{12.5}B_{15}$ amorphous wire (having a diameter of 30 μm and a length of 20 mm; an amorphous wire having a diameter of 130 μm made by a rotational underwater rapid quenching method is drawn, and heated at 475° C. for two minutes while applying a tensile force of 4 kg/mm², then rapidly cooled to room temperature to make the amorphous wire having a magnetostriction of $-3 \times 10^{-6}$). A sinusoidal AC power source 12 is connected to the amorphous wire 11. Reference numeral 13 denotes an internal resistor for maintaining a constant amplitude of AC current.

FIG. 5 shows measurement results of an amplitude Em of a voltage across the amorphous wire when a sinusoidal AC current of a frequency f and an amplitude of 15 mA is supplied from the sinusoidal AC power source 12 while applying a tensile force to the amorphous wire 11.

As is obvious from the chart, when a tensile force F of about 6 kg/mm² [60 MPa (megapascal)] is applied to the amorphous wire 11, the amplitude Em of the voltage across the amorphous wire 11 increased within a frequency range of the frequency f from 50 kHz to 1 MHz, while it decreased in the range from 1 MHz to about 20 MHz. It is seen that the amplitude Em of the voltage across the amorphous wire 11 increases as the frequency f increases at 50 kHz or more, indicating that the amorphous wire 11 exhibits skin effect.

Figure 6:
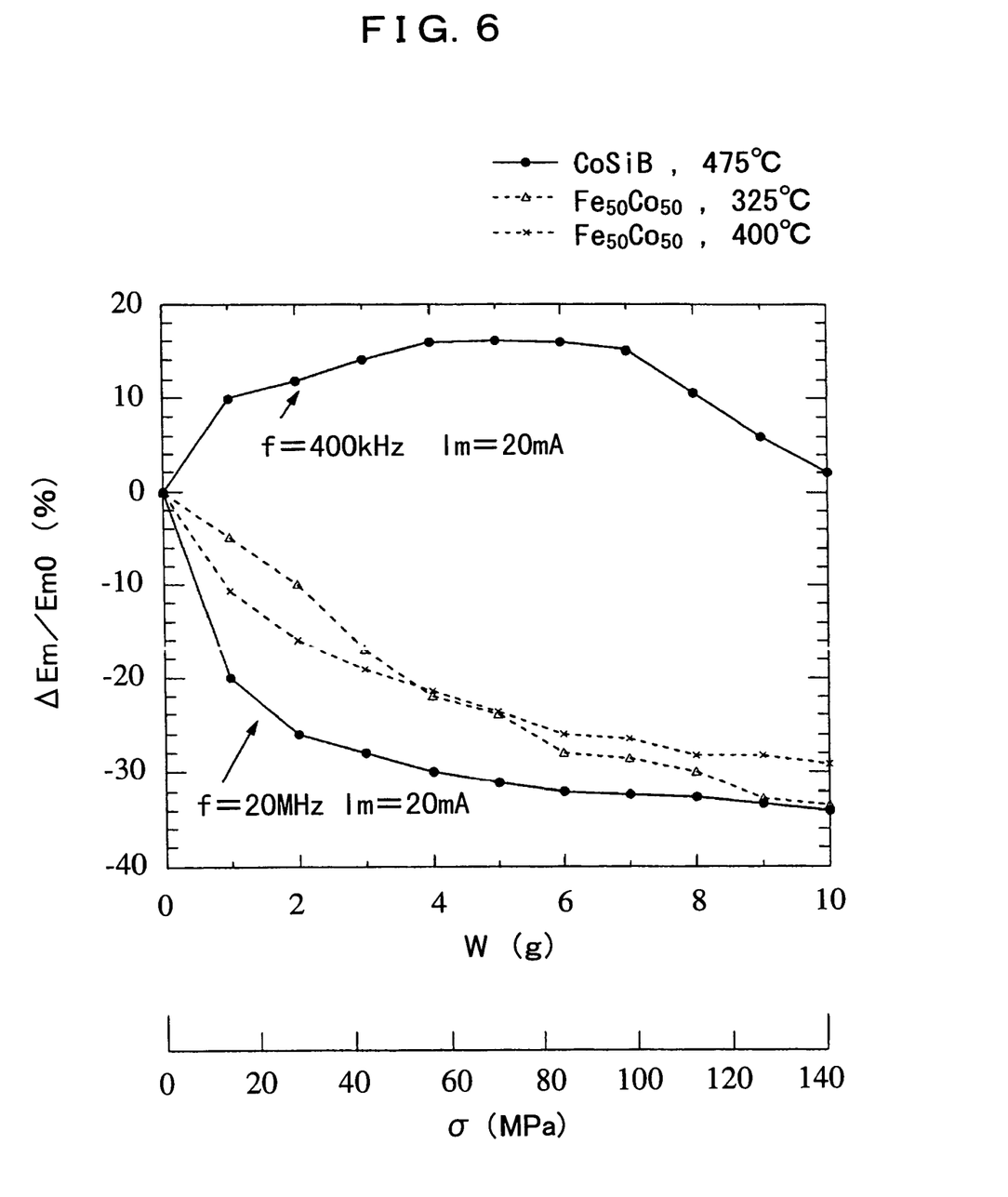
FIG. 6 is a chart showing changes in voltage amplitude caused by stress of the high-sensitivity stress detector in accordance with the present invention (Part 2).

FIG. 6 shows changes in voltage amplitude (part 2) caused by stress at f=400 kHz and 20 MHz, respectively, in the aforementioned high-sensitivity stress detector.

The present embodiment shows measurement results of changes in the amplitude Em of the voltage across wires when sinusoidal currents of 400 kHz and 20 MHz, respectively, and an amplitude of 20 mA are supplied to the CoSiB amorphous wire used in the measurement, the results of which being shown in FIG. 5, and an amorphous wire having positive magnetostriction [$(Fe_{0.5}Co_{0.5})_{72.5}Si_{12.5}B_{15}$; 30 μm in diameter; 20 mm in length; Magnetostriction=$5 \times 10^{-6}$] while applying a tensile load W to the wires.

When f=20 MHz, the amplitude Em in the voltage across the wire decreases by 20% under a 1-gram load (13 MPa tensile force) in the case of the CoSiB wire. The CoSiB amorphous wire has a maximum tensile strength of 306 MPa and a maximum distortion (elongation) of 3.4%, so that its distortion gauge factor (change in electromagnetic amount/elongation) will be 1286. This is an extremely high value, namely, about 6.5 times the gauge factor of about 200 of a conventional semiconductor distortion gauge having highest sensitivity. The CoSiB amorphous wire having a 20 μm diameter exhibited a gauge factor of 4000. The FeCoSiB wire exhibited a gauge factor of about 400, indicating that thin amorphous wires provided with tensile annealing exhibit markedly high gauge factors.

Figure 7:
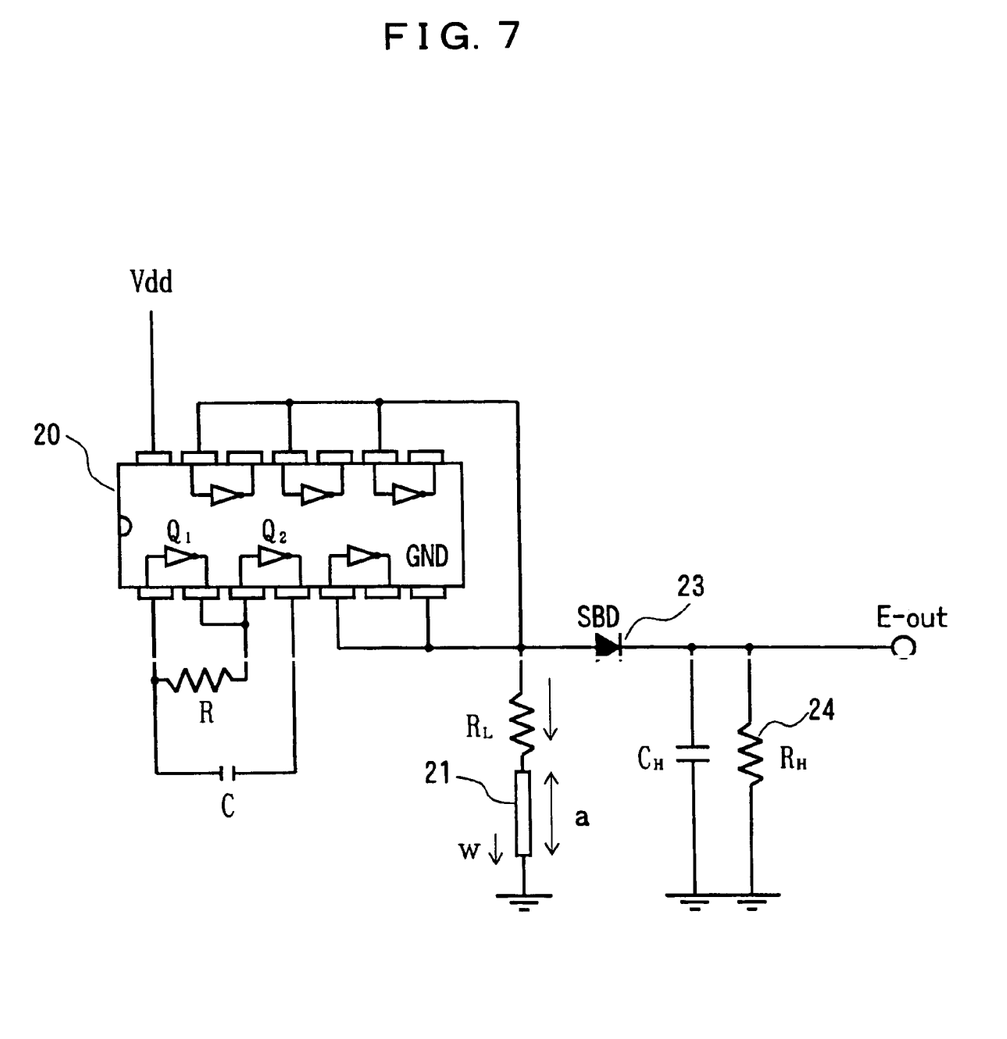
FIG. 7 is a configuration diagram of the high-sensitivity stress detector in accordance with the present invention.
Figure 8:
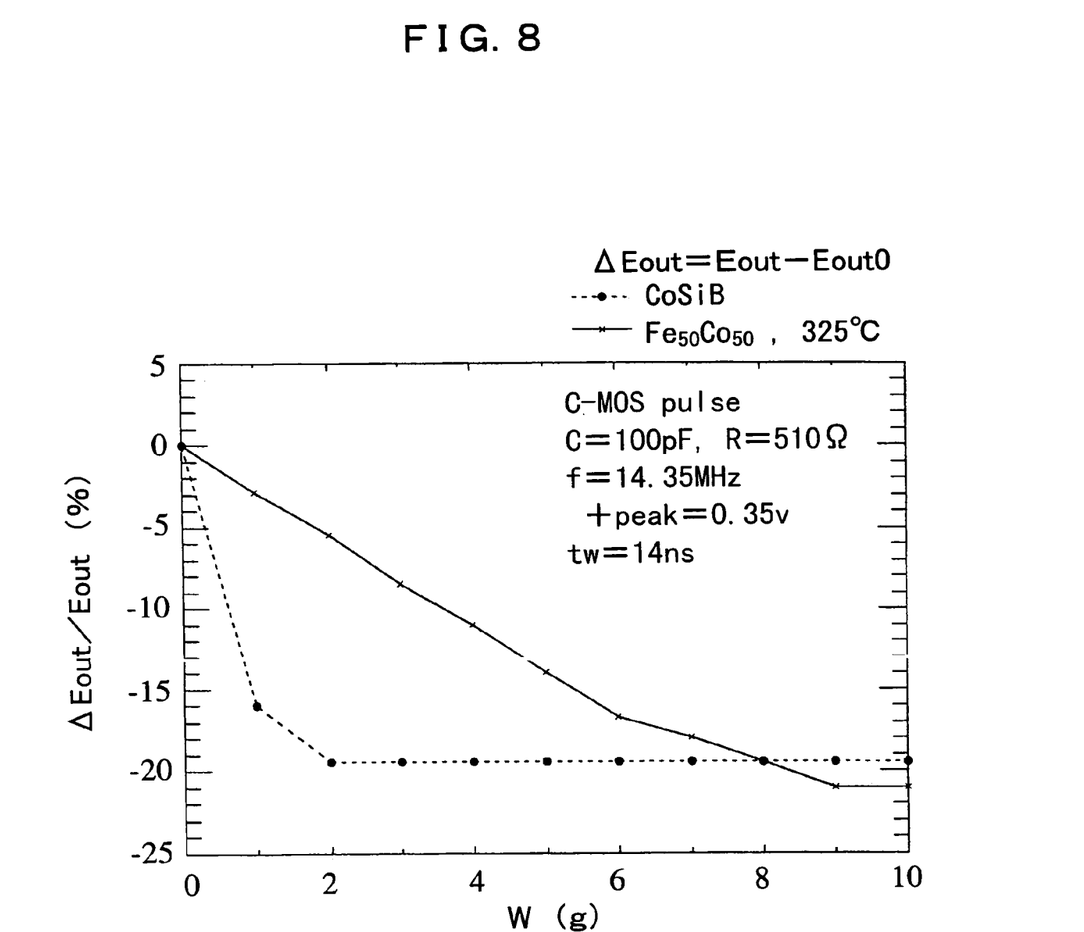
FIG. 8 is a chart showing stress detection results of the high-sensitivity stress detector (stress sensor) in accordance with the present invention.

FIG. 7 is a configuration of a high-sensitivity stress detector in accordance with the present invention, and FIG. 8 shows the stress detection results of the high-sensitivity stress detector (stress sensor).

An induced pulse voltage of an amorphous wire 21 is converted into a DC voltage E-out as an output voltage by an RC peak holding circuit 24, using a Schottky barrier diode SBD 23 as a buffer. Incidentally, an IC chip 20 is comprised of 74AC04. R denotes 20 KΩ, C denotes 100 pF, $R_L$ denotes 10 Ω, $C_H$ denotes 1000 pF, and $R_H$ denotes 510 kΩ.

If an oscillation frequency is 14.35 MHz, a pulse width is 14 ns (nanosecond), and a pulse current height is 30 mA, then an output voltage Eout decreases by 15% under the 1-gram load. The gauge factor of the stress sensor is about 960, which is about five times the gauge factor 200 of a semiconductor strain gauge. If the FeCoSiB wire is used for a head, the gauge factor is about 170, but stress detection characteristics show high linearity and a wide dynamic range of 6 g (82 MPa) is observed.

The following will explain characteristics of the present invention.

Figure 1:
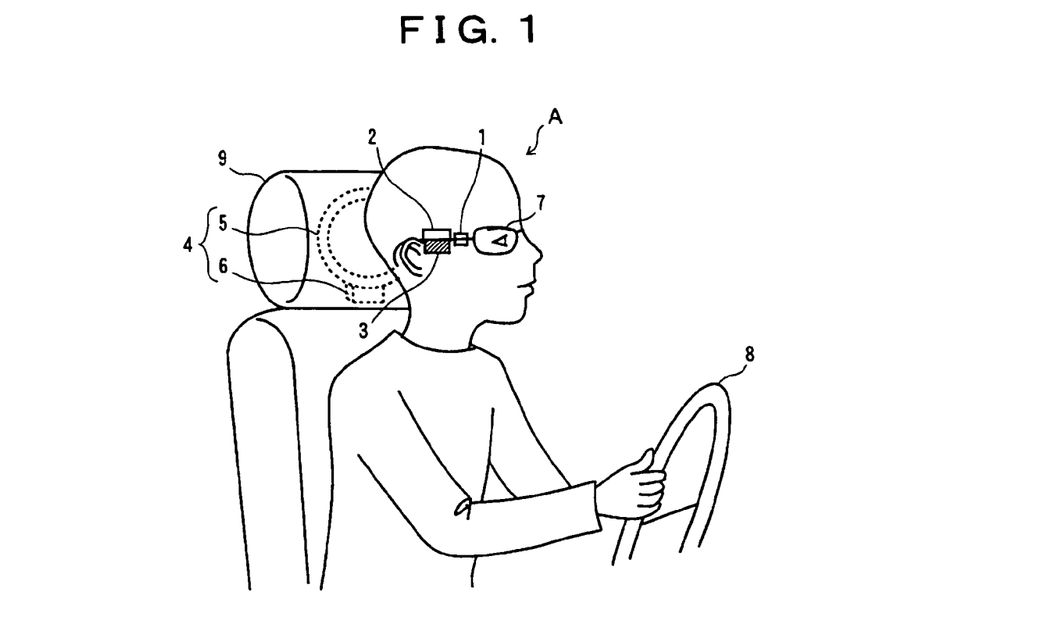
FIG. 1 is a schematic diagram of a drowse detection and waking system for a vehicle driver that shows an embodiment of the present invention.
Figure 2:
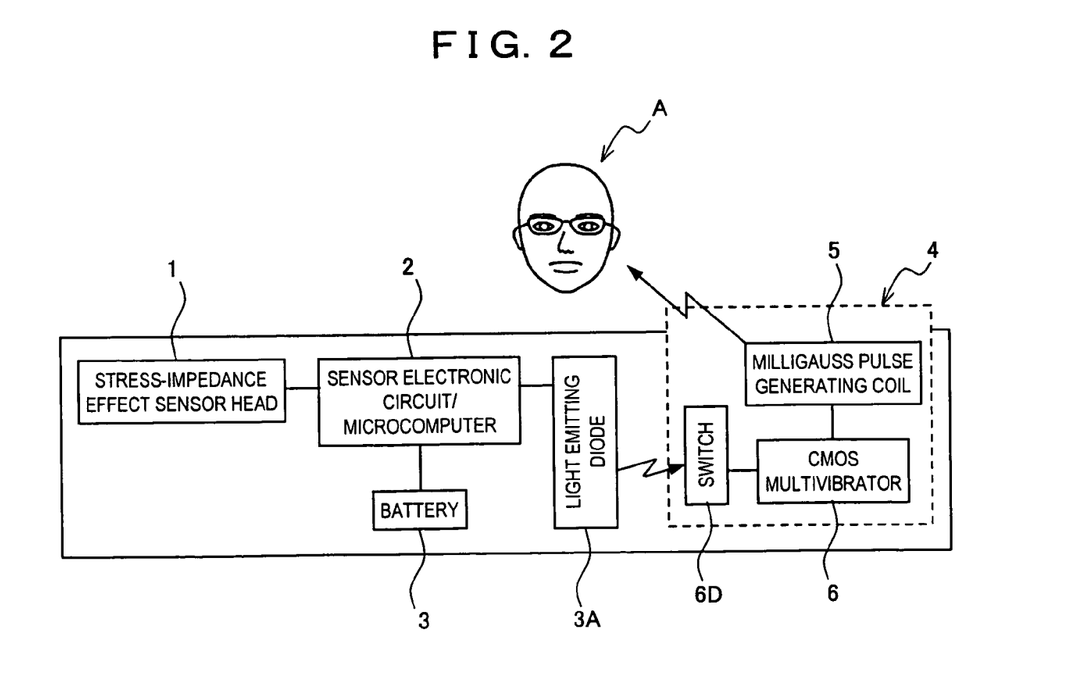
FIG. 2 is a block diagram of the drowse detection and waking system for a vehicle driver that shows the embodiment of the present invention.

FIG. 1 is a diagram showing a constitution example of a drowse detection and waking system for a vehicle driver, which illustrates an embodiment of the present invention. FIG. 2 is a block diagram of the drowse detection and waking system for a vehicle driver.

In these figures, reference numeral 1 denotes a stress-impedance effect sensor head, reference numeral 2 denotes a sensor electronic circuit/microcomputer (8-bit microcomputer), reference numeral 3 denotes a battery, reference numeral 3A denotes a light emitting diode, reference numeral 4 denotes a waking milligauss ultra-low frequency generator disposed in a pillow 9 of a driver's seat, reference numeral 5 denotes its milligauss pulse generating coil, reference numeral 6 denotes a CMOS multivibrator, reference numeral 6D denotes a switch for driving the CMOS multivibrator 6 upon receipt of light from the light emitting diode 3A, reference numeral 7 denotes a temple bow of a glasses frame of a driver A, reference numeral 8 denotes a vehicular steering wheel, and reference numeral 9 denotes the pillow of the driver's seat.

A high-density mounting type or IC type amorphous magnetostrictive wire stress-impedance effect sensor head 1 is secured to the temple bow 7 of the glasses frame of the driver A. The head 1 is a 15 mm-diameter cylindrical sensor head having its surface provided with a CoSiB negative magnetostrictive amorphous wire of a 20-micron diameter. The head 1 is lightly pressed against the vicinity of a temple of the head of the driver A.

The stress-impedance effect sensor head 1 detects a skin deformation stress caused by eye muscle contraction from a blink, and a blink waveform is supplied to the microcomputer 2 secured to the temple bow 7 of the glasses frame of the driver A. If information processing by the microcomputer 2 indicates that eyelids have closed for 0.4 seconds or more, then it is determined as heavy drowsiness.

The stress-impedance effect sensor head 1 incorporates a CMOS circuit to perform pulse operations, power consumption being about 5 milliwatts. The microcomputer 2 performs a light level of operation, power consumption being about 20 milliwatts. Hence, a button battery may be used for the battery 3. The stress-impedance effect sensor 1 performs intermittent detection, e.g., performs a detecting operation for 2 seconds at intervals of 5 seconds.

The waking device illustrating an embodiment of the present invention will now be explained.

Figure 3:
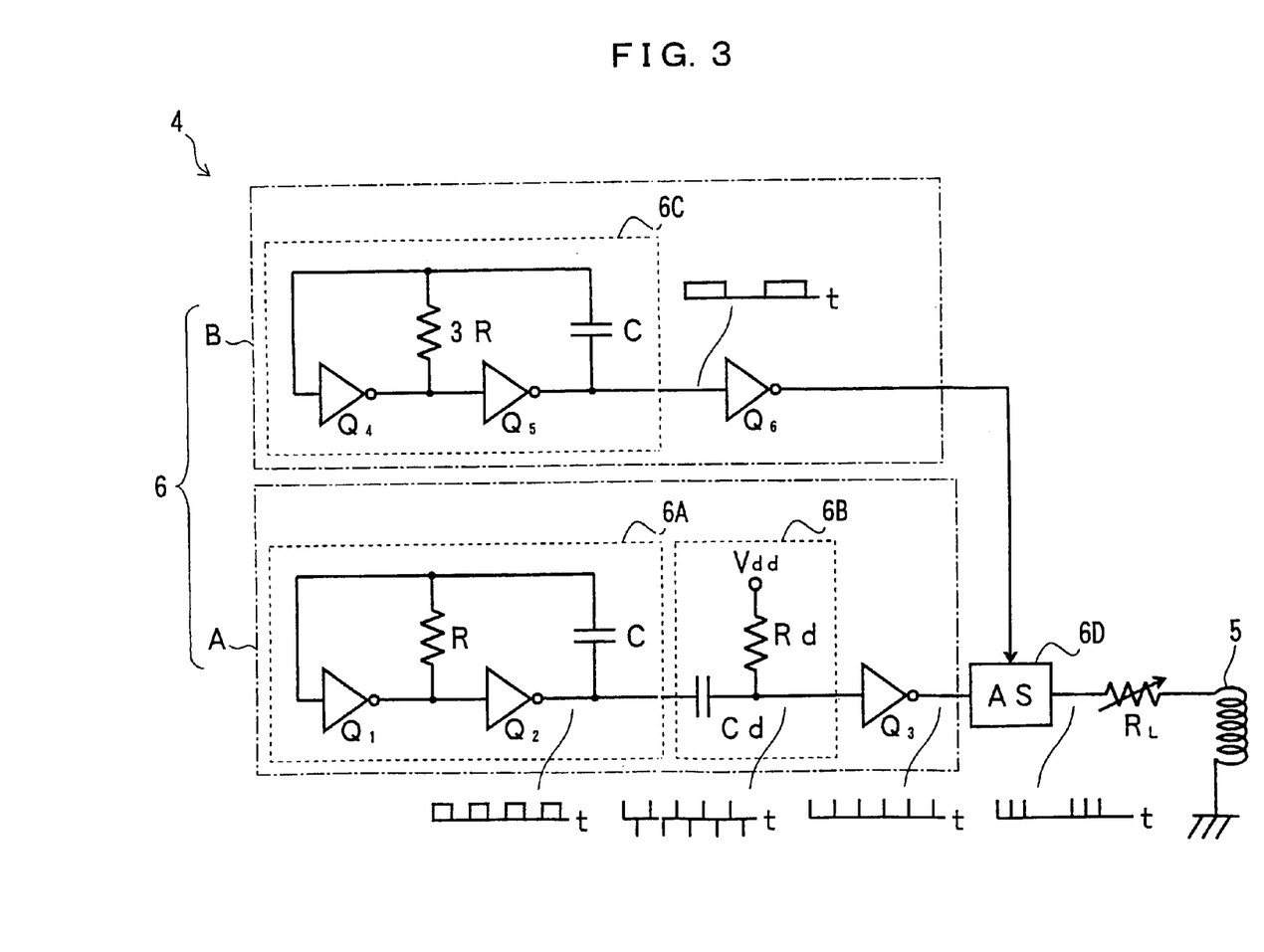
FIG. 3 is a diagram showing a configuration of a milli-gauss ultra-low frequency wave generator for waking in accordance with the present invention.

FIG. 3 is a diagram showing a configuration of a milligauss ultra-low frequency generator for waking in accordance with the present invention.

In the figure, reference numeral 4 denotes a waking milligauss ultra-low frequency generator, reference numeral 5 denotes a coil for generating a milligauss ultra-low frequency AC magnetic field, and reference numeral 6 denotes a CMOS multivibrator serving as a driving circuit of the coil for generating a milligauss ultra-low frequency AC magnetic field. The driving circuit 6 includes a circuit A and a circuit B.

The circuit A (pulse voltage generator circuit) is constructed of a square-wave voltage oscillator circuit (multivibrator) 6A having two CMOS inverters $Q_1$ and $Q_2$, R and C, a differentiating circuit ($R_d$, $C_d$) 6B that converts an oscillation voltage from the square-wave voltage oscillator circuit (multivibrator) 6A into a pulse voltage, and a CMOS inverter $Q_3$ for shaping and amplifying the pulse voltage of the differentiating circuit 6B. An oscillation frequency f is expressed as f=0.1/RC[Hz], and R=50 kΩ and C=5 to 50 μF are used to obtain 1 to 10 Hz.

The circuit B is constructed of a square-wave voltage oscillator circuit (multivibrator) 6C having two CMOS inverters $Q_4$ and $Q_5$, 3R and C, and a CMOS inverter $Q_6$ for shaping and amplifying the square-wave voltage. The circuit B is a square-wave oscillator circuit having an oscillation frequency of about 0.5 Hz and adapted to close an analog switch AS6D by an output voltage at a half cycle of its positive voltage so as to apply a pulse current of the circuit A to a coil 5 for generating a milligauss ultra-low frequency AC magnetic field. Thus, the milligauss pulse magnetic field is generated.

More specifically, in the waking milligauss ultra-low frequency generator 4, when a drowsiness signal is received from the microcomputer 2, the light emitting diode 3A is driven to emit light, causing the switch (light-responsive switch) 6D to turn on. This in turn drives the CMOS multivibrator 6 to supply a 5-mA, 4-Hz current to the 100-turn milligauss pulse generating coil 5 having a diameter of 12 cm. Thus, the milligauss ultra-low frequency generator 4 has a simple construction using the CMOS multivibrator circuit 6, and consumes about 1 milliwatt, so that it can be operated many times using two AAA-size batteries.

The waking principle is innovative. A milligauss AC magnetic field causes in vivo water molecule clusters and vital ions to develop cyclotron resonance in geomagnetism. A standing wave loop of proton exchange is produced to provide a molecular self organizing nucleus, promoting the activation of vital activities of a living body thereby waking dormant brain up.

Hence, the milligauss AC magnetic field generating coil 5 is preferably installed in a driver's seat pillow 9 or a cap (not shown) on a driver (user) so that it is near the brain.

The milligauss generation may be performed for, e.g., 10 seconds at 5-minute intervals rather than being operatively connected to the stress-impedance effect sensor 1.

A small milligauss pulse generating coil may be secured to a temple bow of a glasses frame to apply a magnetic field to a temple, or a microminiature sound wave generator or vibrator that has a waking function may be attached to a temple bow of a glasses frame.

It is to be understood that the present invention is not limited to the aforementioned embodiment. To the contrary, the present invention is intended to cover various modifications included within the spirit and scope thereof.

As explained above in detail, the following advantages can be obtained by present invention:

(A) It is possible to provide a prompt, accurate and highly practical drowsiness detecting device and a waking device operatively connected thereto.

(B) In particular, the supersensitive stress sensor improved for practical use is secured onto a glasses frame such that a sensor head thereof is pressed against the vicinity of a temple of a driver's head. With this arrangement, eyelid motions can be detected without attaching magnets on eyelids and drowsiness is determined by a microcomputer.

(C) Furthermore, the principle that is utterly different from a conventional waking method is used for waking up a vehicle driver. This makes it possible to wake up the driver by applying a minute AC magnetic field in a milligauss order to activate the driver's in vivo water molecules or vital ions.

(D) It is possible, for example, to detect drowsiness of a vehicle driver or the like and to wake the driver up before his/her drowse leads to a traffic accident.

(E) The drowsiness detecting and waking device may be integrally mounted on a glasses frame.

INDUSTRIAL APPLICABILITY

The drowsiness detecting device and the waking device operatively connected to the same according to the present invention make it possible to prevent traffic accidents when they are installed in a vehicle and onto a driver, or to contribute to prevention of industrial accidents when they are installed onto a security monitoring system and security surveillance personnel at a plant. Thus, an extensive range of applications can be expected of the devices in accordance with the present invention.

The invention claimed is:

1. A drowsiness detecting and waking device comprising:
   (a) a high-sensitivity stress sensor combining stress-impedance effect of an amorphous magnetostrictive wire and a CMOS multivibrator circuit attached to a temple bow of a glasses frame at a position thereof in the vicinity of a temple of a user;
   (b) a microcomputer that detects a blinking motion of eyelids of the user from information supplied from the high-sensitivity stress sensor and determines the drowsiness of the user on the basis of the detected information; and
   (c) a milligauss ultra-low frequency AC magnetic field generator driven on the basis of a drowsiness signal from the microcomputer, wherein a magnetic field generated by the milligauss ultra-low frequency AC magnetic field generator is applied to the brain of the user.

2. The drowsiness detecting and waking device according to claim 1, wherein a coil and a driving circuit for generating the milligauss ultra-low frequency AC magnetic field are disposed in the vicinity of the brain of the user.

3. The drowsiness detecting and waking device according to claim 1, wherein a coil and a driving circuit for generating the milligauss ultra-low frequency AC magnetic field are disposed in the vicinity of a temple of the user.

* * * * *